(12) United States Patent
Armer et al.

(10) Patent No.: US 12,268,593 B2
(45) Date of Patent: Apr. 8, 2025

(54) VALVE ANCHOR AND INSTALLATION METHOD

(71) Applicant: Edwards Lifesciences Corporation, Irvine, CA (US)

(72) Inventors: Dustin P. Armer, Costa Mesa, CA (US); Sean Chow, Tustin, CA (US); Jenny Nguyen, Huntington Beach, CA (US); Emil Karapetian, Huntington Beach, CA (US); Tri D. Tran, Fountain Valley, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 824 days.

(21) Appl. No.: 17/334,464

(22) Filed: May 28, 2021

(65) Prior Publication Data

US 2021/0282923 A1     Sep. 16, 2021

Related U.S. Application Data

(63) Continuation of application No. 16/691,244, filed on Nov. 21, 2019, now Pat. No. 11,026,781, which is a
(Continued)

(51) Int. Cl.
*A61F 2/24*     (2006.01)
(52) U.S. Cl.
CPC .......... *A61F 2/2409* (2013.01); *A61F 2/2418* (2013.01); *A61F 2/2457* (2013.01);
(Continued)

(58) Field of Classification Search
CPC ..... A61F 2/2418; A61F 2/2409; A61F 2/2457
See application file for complete search history.

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 0144167 C | 9/1903 |
| DE | 2246526 A1 | 3/1973 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.
(Continued)

*Primary Examiner* — Suba Ganesan
(74) *Attorney, Agent, or Firm* — Klarquist Sparkman, LLP; Linda Allyson Nassif (57) ABSTRACT

Anchor devices and methods used to secure a prosthetic valve to a native valve annulus are described. The anchor device can be a separate expandable element from the prosthetic valve that is first advanced to the annulus and deployed, after which an expandable prosthetic valve is advanced to within the annulus and deployed. The combination of the two elements can apply a clamping force to the valve leaflets which holds the prosthetic valve in place. The anchor device can have a lower or ventricular portion and an upper or atrial portion. The anchor device can include one or more leaflet clamping portions. One, two, or more upstanding vertical posts between the clamping portions can extend upward at the valve commissures and support the upper portion, which can include one or more structures for leak prevention.

20 Claims, 9 Drawing Sheets

Related U.S. Application Data continuation of application No. PCT/US2018/033086, filed on May 17, 2018.

(60) Provisional application No. 62/509,278, filed on May 22, 2017.

(52) U.S. Cl.
CPC ............... A61F 2220/0008 (2013.01); A61F 2230/0056 (2013.01); A61F 2250/001 (2013.01)

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |

(56) References Cited

U.S. PATENT DOCUMENTS

| | | |
|---|---|---|
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,439,970 B2 | 5/2013 | Jimenez et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0239265 A1* | 10/2007 | Birdsall .............. A61L 27/303 623/2.11 |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2010/0249911 A1 | 9/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2012/0323313 A1* | 12/2012 | Seguin .............. A61F 2/246 623/2.14 |
| 2013/0023985 A1 | 1/2013 | Khairkhahan et al. |
| 2013/0046373 A1 | 2/2013 | Cartledge et al. |
| 2013/0116779 A1* | 5/2013 | Weber .............. A61F 2/2442 623/2.18 |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0253635 A1 | 9/2013 | Straubinger et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277390 A1* | 9/2014 | Ratz .............. A61F 2/2418 623/1.26 |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |

(56) References Cited

U.S. PATENT DOCUMENTS

| | | | |
|---|---|---|---|
| 2016/0030169 A1* | 2/2016 | Shahriari | A61F 2/2418 623/2.18 |
| 2016/0051362 A1 | 2/2016 | Cooper et al. | |
| 2016/0374802 A1 | 12/2016 | Levi et al. | |
| 2017/0014229 A1 | 1/2017 | Nguyen-Thien-Nhon et al. | |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Levi et al. | |
| 2019/0192289 A1 | 6/2019 | Levi et al. | |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013075215 A1 | 5/2013 |
| WO | 2013106585 A1 | 7/2013 |
| WO | 2015085218 A1 | 6/2015 |

OTHER PUBLICATIONS

Bailey, S. "Percutaneous Expandable Prosthetic Valves," Textbook of Interventional Cardiology vol. 2, 2nd Ed. pp. 1268-1276. 1994.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: In vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Wheatley, "Valve Prostheses," Operative Surgery, 4th ed. pp. 415-424. 1986.

* cited by examiner

VALVE ANCHOR AND INSTALLATION METHOD

CROSS-REFERENCE TO RELATED APPLICATIONS

This application is a continuation of U.S. application Ser. No. 16/691,244, filed Nov. 21, 2019, which is a continuation of PCT/US2018/033086, filed May 17, 2018, which claims the benefit of U.S. Provisional Application No. 62/509,278, filed May 22, 2017. These applications are incorporated herein by reference in their entirety.

FIELD OF THE INVENTION

The present invention relates to repairing or replacing a native valve, including to devices for anchoring or docking a prosthetic valve at a native valve and a corresponding installation methods.

BACKGROUND OF THE INVENTION

The heart is a hollow muscular organ having four pumping chambers separated by four heart valves: aortic, mitral (or bicuspid), tricuspid, and pulmonary. Heart valves are comprised of a dense fibrous ring known as the annulus, and flexible tissue leaflets or cusps attached to the annulus.

Heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, where the prosthetic valve is sutured in place while the patient is on cardiopulmonary bypass. Such surgeries are time-consuming, dangerous and prone to complication.

Less invasive transvascular and transapical techniques can be used for introducing and implanting a prosthetic heart valve off-pump and while the heart is beating. For example, a prosthetic valve can be mounted in a crimped state on the end portion of a flexible catheter and advanced through a blood vessel of the patient until the valve reaches the implantation site. The valve at the catheter tip can then be expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter. These are sutureless techniques which can greatly reduce the procedure time.

One issue with sutureless valves is the potential for valve migration. For example, when an aortic prosthetic valve is deployed, a 100-200 mmHg pressure can load on the aortic valve immediately. The pressure times the valve surface area can produce a substantial load force on the prosthetic valve and might cause valve migration towards the aortic arch.

Treatment of the mitral valve can present additional challenges, and methods and apparatuses appropriate for the aortic valve may not be well suited for use with the mitral valve. For instance, the mitral valve includes clusters of chordae tendineae extending from the valve leaflets to the walls of the ventricle that may interfere with placement of the prosthesis. The shape of the mitral valve, rather than being circular and uniform like the aortic valve, can be an oval or kidney-like shape that may not be well suited for supporting conventional stents of cylindrical configuration. Further, whereas the aortic valve annulus is often entirely surrounded by muscular tissue, the mitral valve annulus may be bounded by muscular tissue on the outer (posterior) wall only. The anterior side of the mitral valve annulus is bounded by a thin vessel wall adjacent the left ventricular outflow tract ("LVOT"), which must remain open to allow blood to pass into the aorta. As a result, the stent-type fixation may not be suitable for the mitral valve because the anterior side of the native valve has insufficient radial strength and can distort, risking occlusion of the left ventricular outflow tract. Moreover, mitral valve disease often is accompanied by (or caused by) gradual enlargement of the native annulus and/or the left ventricle. Thus, treatment approaches which rely upon radial engagement with or outward compression against the native annulus can be subject to failure as the size and shape of the annulus changes.

Despite certain advances, there remains a need for improved methods, systems, and apparatus for implanting prosthetic heart valves to the mitral annulus.

SUMMARY OF THE INVENTION

This summary is meant to provide examples and is not intended to be limiting of the scope of the invention in any way. For example, any feature included in an example of this summary is not required by the claims, unless the claims explicitly recite the features. Also, the features described here and elsewhere in the application can be combined in a variety of ways.

The present application discloses embodiments of an anchor device and methods used to secure a prosthetic heart valve to a native heart valve annulus. The anchor device can be a separate expandable element from the heart valve prosthesis that can be first advanced to the native annulus and deployed, after which an expandable heart valve prosthesis can be advanced to within the native annulus and/or anchor device and deployed. The combination of an anchor device and heart valve prosthesis can apply a clamping force to the heart valve leaflets which holds the prosthetic heart valve in place.

The anchor device can have a lower portion (e.g., a ventricular portion disposable/positionable in the left ventricle) and an upper portion (e.g., an atrial portion disposable/positionable in the left atrium). The lower portion can include one or more leaflet clamping portions, for example, two leaflet clamping portions opposite one another that are positioned radially outside the native valve leaflets. One, two, or more upstanding vertical posts between the clamping portions can extend upward at the valve commissures and support the upper portion, which can include one or more structures for leak prevention.

Anchor devices herein can be for securing a prosthetic valve at a native valve (e.g., a native valve between an atrium and a ventricle such as a mitral or tricuspid valve). The Anchor devices can comprise a lower or ventricular portion and an upper or atrial portion. The lower or ventricular portion can be below the upper or atrial portion. The lower or ventricular portion can have an expandable tubular body about a vertical axis and can comprise struts (e.g., undulating struts). The tubular body can define one, two, three, or more leaflet clamping portions (e.g., two leaflet clamping portions opposite one another). Each can be defined by at least one peak extending upward. There can also be a downward valley on opposite sides of the lower or ventricular portion or the peak (e.g., between two leaflet clamping portions). The anchor device can be configured to receive and/or optionally include an expandable prosthetic valve expanded within the anchor device.

The anchor devices can further include one or more upstanding vertical posts, for example, an upstanding vertical post commencing at each valley of the undulating struts and extending upward beyond a maximum height of the peaks of the two leaflet clamping portions and terminating in the upper or atrial portion. The vertical posts can be located less than 180° from each other around a circumference of the anchor device (e.g., if only two posts are used, they can but do not need to be 180° apart). The upper or atrial portion can include an annular ring of porous material attached to top ends of the vertical posts. The annular ring of porous material can be selected from the group consisting of polyester fabric, porous polymer material, ePTFE, foam, other materials, or some or all of the foregoing. The upper or atrial portion can include a pair of Y-shaped struts at a terminal end of each vertical post, which can optionally include a cover. The atrial portion can include a wire ring at a terminal end of each vertical post, which can optionally include a cover.

The clamping portions can each include at least two peaks and one valley therebetween. The clamping portions can be covered (e.g., with fabric, a coating, a polymer material, and/or other material).

Each strut can have a variety of shapes, the same or different. As one example each strut can include an undulating S-shape and terminate in an asymptotic manner at each end at a peak and a valley. The struts can also define a sinusoidal pattern.

The lower or ventricular portion can include one or more integrally formed downwardly extending legs that terminate below the valleys in buckles to facilitate manipulation and deployment of the anchor device. The legs can each extend downward from one of the peaks of the clamping portions. In one embodiment, there are three of the legs and three buckles. The buckles can form squares or rectangles or another shape with a hole therethrough.

Additional features and/or components described elsewhere herein can also be used.

Methods herein (e.g., a beating heart method) can be for securing a prosthetic valve at a native valve (e.g., a native valve between an atrium and a ventricle). The native valve has native leaflets (and, optionally, attached chordae in the ventricle), and commissures between the leaflets at a native annulus of the native valve. The Methods can comprise advancing an anchor device to the native valve, the device having a lower (e.g., ventricular) portion and an upper (e.g., atrial) portion. The lower or ventricular portion can have an expandable tubular body about a vertical axis comprising undulating struts.

In one embodiment, the tubular body has two leaflet clamping portions opposite one another. The two leaflet clamping portions each defined by at least one peak and two valleys in between the two leaflet clamping portions. The anchor device further including two upstanding vertical posts each commencing at a separate valley of the undulating struts and extending upward beyond a maximum height of the peaks of the two leaflet clamping portions and terminating in the upper or atrial portion. The anchor device struts can be Nitinol, and each clamping portion can have at least two peaks and one valley therebetween. The clamping portions can be covered with fabric.

The atrial portion can be formed in a variety of ways. For example, the atrial portion can comprise a tubular foam member. The atrial portion can also include a pair of Y-shaped struts at a terminal end of each vertical post. A fabric cover can be included across each pair of Y-shaped struts. Optionally, the atrial portion includes a wire ring at a terminal end of each vertical post. A cover can be included across the wire rings.

The methods can also comprise expanding the lower or ventricular portion of the device below the annulus (e.g., in a ventricle) and positioning the two leaflet clamping portions radially outside respective leaflets of the native leaflets. The methods can also comprise positioning the upstanding posts such that they project upward at valve commissures (e.g., two upstanding posts at two valve commissures) and support the upper or atrial portion above the native annulus (e.g., in the atrium).

The methods can also comprise advancing an expandable prosthetic valve to within the native leaflets and expanding to compress the native leaflets outward against the leaflet clamping portions of the device. Optionally, the anchor device and prosthetic valve can be deployed using one access or delivery system or two separate access or delivery systems.

Additional steps described elsewhere herein can also be used, and the steps of the methods can be reordered.

A system for securing a prosthetic valve at a native valve can comprise an expandable/collapsible anchor device having a first portion or lower portion below a second portion or an upper portion, the first or lower portion having an expandable tubular body about a vertical axis and comprising struts (e.g., undulating struts, etc.), the tubular body defining a leaflet clamping portion defined by at least one peak extending upward, wherein there is a downward valley on the first or lower portion adjacent the at least one leaflet clamping portion, the device further including an upstanding vertical post commencing at the downward valley and extending upward beyond a maximum height of the at least one peak of the leaflet clamping portion and terminating in the second or upper portion.

The system can also include one or more additional leaflet clamping portions (e.g., a second leaflet clamping portion). The leaflet clamping portions can be defined by at least one peak or more than one peak extending upward. In one embodiment, the clamping portions each include at least two peaks and one valley therebetween. The leaflet clamping portion(s) can be covered with fabric.

The struts can take on a variety of shapes and configurations. In one embodiment, the device includes undulating struts and each undulating strut has an S-shape and terminates in an asymptotic manner at each end at a peak and a valley.

The system can include one or more additional vertical posts (e.g., a second upstanding vertical post). In one embodiment, the vertical posts commence at a second downward valley and extend upward beyond a maximum height of the at least one peak of the leaflet clamping portion and terminating in the second or upper portion. The vertical posts can be located less than 180° from each other around a circumference of the anchor device. This can be beneficial when native commissures are not located 180° apart from each other, for example, as installed in a mitral valve.

The lower portion can include one or more integrally formed downwardly extending legs that terminate below the valleys in buckles to facilitate manipulation and deployment of the anchor device. In one embodiment, at least one of the legs extends downward from the at least one peak of the leaflet clamping portion. In one embodiment, there are three of the downwardly extending legs and buckles. The buckles can form squares or rectangles or another shape with a hole therethrough.

The second or upper portion can include an annular ring of porous material attached to top end of the vertical post. The annular ring of porous material can be selected from the group consisting of polyester fabric, porous polymer material, ePTFE, and foam or another material. The second or upper portion can include a pair of Y-shaped struts at a terminal end of each vertical post. A fabric cover can be included across each pair of Y-shaped struts. The second or upper portion can include a wire ring at a terminal end of each vertical post. A fabric cover can be included across the wire rings.

The system can also include an expandable prosthetic heart valve, which can be expanded within the anchor device.

Additional features and/or components described elsewhere herein can also be used.

The methods herein (e.g., methods of securing a prosthetic valve at a native valve) can comprise advancing an anchor device to the native valve. The anchor device can be the same as or similar to other anchor devices described elsewhere herein. For example the anchor device can have a first portion or lower portion and a second portion or upper portion. The first or lower portion can have an expandable tubular body about a vertical axis comprising struts (e.g., undulating struts). The tubular body can have one or more leaflet clamping portions. A leaflet clamping portion can be defined by at least one peak and valleys adjacent the at least one peak. The anchor device can further include one or more upstanding vertical posts. An upstanding vertical post can commence at a valley of the undulating struts and extend upward beyond a maximum height of the at least one peak of the leaflet clamping portion and terminating in the second or upper portion. The anchor device struts can be Nitinol, and each clamping portion can have one or more peaks and valleys (e.g., at least two peaks and one valley) therebetween. The clamping portions can be covered with fabric.

The second or upper portion can include a tubular foam member. The second or upper portion can include a pair of Y-shaped struts at a terminal end of each vertical post. A fabric cover can be used across each pair of Y-shaped struts. The second or upper portion can include a wire ring at a terminal end of each vertical post and can include a cover across the wire rings.

The methods can also include expanding the first or lower portion of the device below the native valve or native valve annulus and can include positioning the leaflet clamping portion radially outside at least one leaflet of native leaflets of the native valve. The methods can also include positioning the upstanding vertical post such that it projects upward at a native valve commissure and supports the second or upper portion above the native annulus or the native valve.

The methods can also comprise advancing an expandable prosthetic valve to within the native leaflets and expanding the prosthetic valve to compress the at least one leaflet outward against the leaflet clamping portion.

The methods can include using the same access system or delivery system to deploy the anchor device and the prosthetic valve or using two separate access systems.

Additional steps described elsewhere herein can also be used, and the steps of the methods can be reordered.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 2A and 2B are side and top perspective views of an exemplary anchor device of the present application having an undulating ventricular portion and a tubular leak-preventing atrial portion, while

DETAILED DESCRIPTION OF PREFERRED EMBODIMENTS

The following description and accompanying figures, which describe and show certain embodiments, are made to demonstrate, in a non-limiting manner, several possible configurations of systems, platforms, devices, methods, etc. that may be used for various aspects and features of the present disclosure.

Anchor devices for assisting in implanting a prosthetic heart valve at a native valve (e.g., a mitral valve, tricuspid valve, etc.) are described. An anchor device can be separate from and separately implanted prior to the prosthetic heart valve. Once the anchor device has been installed at the native valve (e.g., mitral valve, etc.), the prosthetic heart valve is delivered and coupled thereto. This process may be accomplished using one combined or two separate catheters, delivery systems/devices, or access systems/devices. While examples are given herein with respect to the mitral valve, use of the devices, systems, methods, etc. described herein is not limited to use with the mitral valve and can be applied in other valves (e.g., aortic valve, pulmonary valve, tricuspid valve) or other locations.

The anchor devices can be used in connection with various types of expandable valves, for example, with a balloon-expandable prosthetic heart valve such as the Edwards SAPIEN 3 Transcatheter Heart Valve (THV) made by Edwards Lifesciences of Irvine, Calif., or such as described in U.S. Pat. No. 6,730,118, which is hereby expressly incorporated herein by reference. However, these exemplary THVs should not be construed as limiting, and embodiments of the disclosed anchor device(s) can be used to secure a wide variety of THVs delivered through a variety of mechanisms (e.g., self-expanding heart valves, other balloon-expanding heart valves, mechanically-expandable heart valves, and the like). The term, "expandable heart valves" is intended to encompass all such varieties.

Exemplary delivery routes through the body and into the heart for both the anchor device(s) and prosthetic heart valve include transvascular (e.g., transfemoral) routes, transapical routes, and transaortic routes, among others. In a transvascular approach, a catheter can be inserted into the vasculature at a site that is relatively distant from the heart. An anchor device or prosthetic valve can be mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Various delivery or access systems having a catheter or sheath can be used. The anchor device and prosthetic heart valve can be deployed using one access system or delivery system for near simultaneous delivery, or with two separate systems for sequential delivery. One delivery system adapted for use in introducing a prosthetic valve into a heart in a transapical procedure is disclosed in U.S. Pat. No. 8,439,970, which is incorporated herein by reference. In a transapical procedure, a prosthetic valve is introduced into the left ventricle through a surgical opening in the apex of the heart. The delivery system in the '970 patent similarly can be used for introducing a prosthetic valve into a heart in a transaortic procedure. In a transaortic procedure, a prosthetic valve is introduced into the aorta through a surgical incision in the ascending aorta, such as through a partial J-sternotomy or right parasternal mini-thoracotomy, and then advanced through the ascending aorta toward heart. Percutaneous or transcatheter delivery systems are also possible.

Figure 1A:
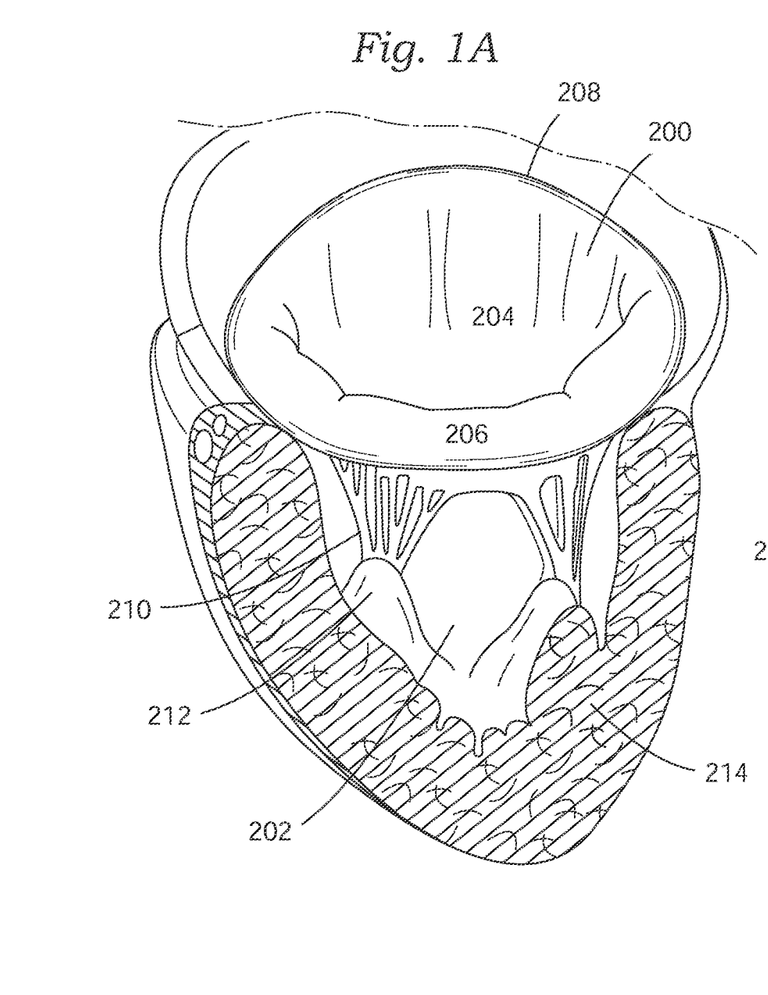
FIG. 1A is a schematic perspective view from the atrial side of a mitral valve and a sectional view of the subvalvular anatomy of the left ventricle.

FIG. 1A is a schematic perspective view from the atrial side of a mitral valve 200 and a sectional view of the subvalvular anatomy of the left ventricle 202. The mitral valve 200 primarily comprises a pair of coapting leaflets—an anterior leaflet 204 and a posterior leaflet 206—secured around their outer edges to a fibrous mitral annulus 208. The inner edges of the anterior and posterior leaflets 204, 206 connect to string-like chordae tendineae 210 that extend down into the left ventricle 202 and are tethered at papillary muscles 212 that extend upward from the muscular myocardium 214 defining the left ventricular cavity. As the main outlet pumping chamber of the heart, the myocardium 214 contracts in systole which reduces tension in the chordae tendineae 210 and permits the leaflets 204, 206 to come together or coapt. Contraction of the volume within the left ventricle 202 sends blood out through the aortic valve (not shown) and into the body. In diastole, the myocardium 214 expands outward pulling the chordae tendineae 210 down in tension to help open the leaflets 204, 206 and pulling blood through the mitral valve 200 to fill the cavity of the left ventricle 202.

Figure 1B:
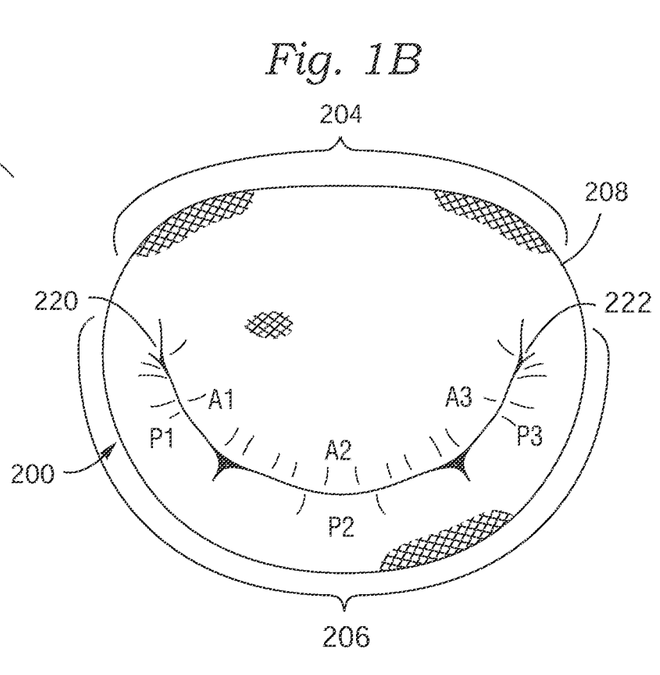
FIG. 1B is an atrial plan view of the mitral valve leaflets indicating common nomenclature initials for regular anatomical features.

FIG. 1B is an atrial plan view of the leaflets 204, 206 of the mitral valve 200. The surrounding mitral annulus 208 is often described as it D-shaped with a somewhat straighter side adjacent the anterior leaflet 204 and a more rounded or convex side adjacent the posterior leaflet 206. The leaflets are shaped such that the line of coaptation resembles a smile that approximately parallels the posterior aspect of the mitral annulus 208. The anterior leaflet 204 spans a smaller peripheral aspect around the mitral annulus 208 than the posterior leaflet 206, but the anterior leaflet 204 has a single cusp with a convex free edge that extends farther into the orifice defined by the mitral annulus 208. Typically, the anterior leaflet 204 has three labeled regions or cusps A1, A2, A3 around its periphery. The posterior leaflet 206, on the other hand, is typically divided by creases into three cusps P1, P2, P3 around its periphery and has a generally concave free edge. Two commissures—an anterior commissure 220 and a posterior commissure 222—generally defined the intersection of the line of coaptation between the two leaflets 204, 206 and the mitral annulus 208. The region at both the anterior commissure 220 and posterior commissure 222 may not be so clear, and sometimes a cusp or leaflet is defined at those points, as will be seen.

Figure 1C:
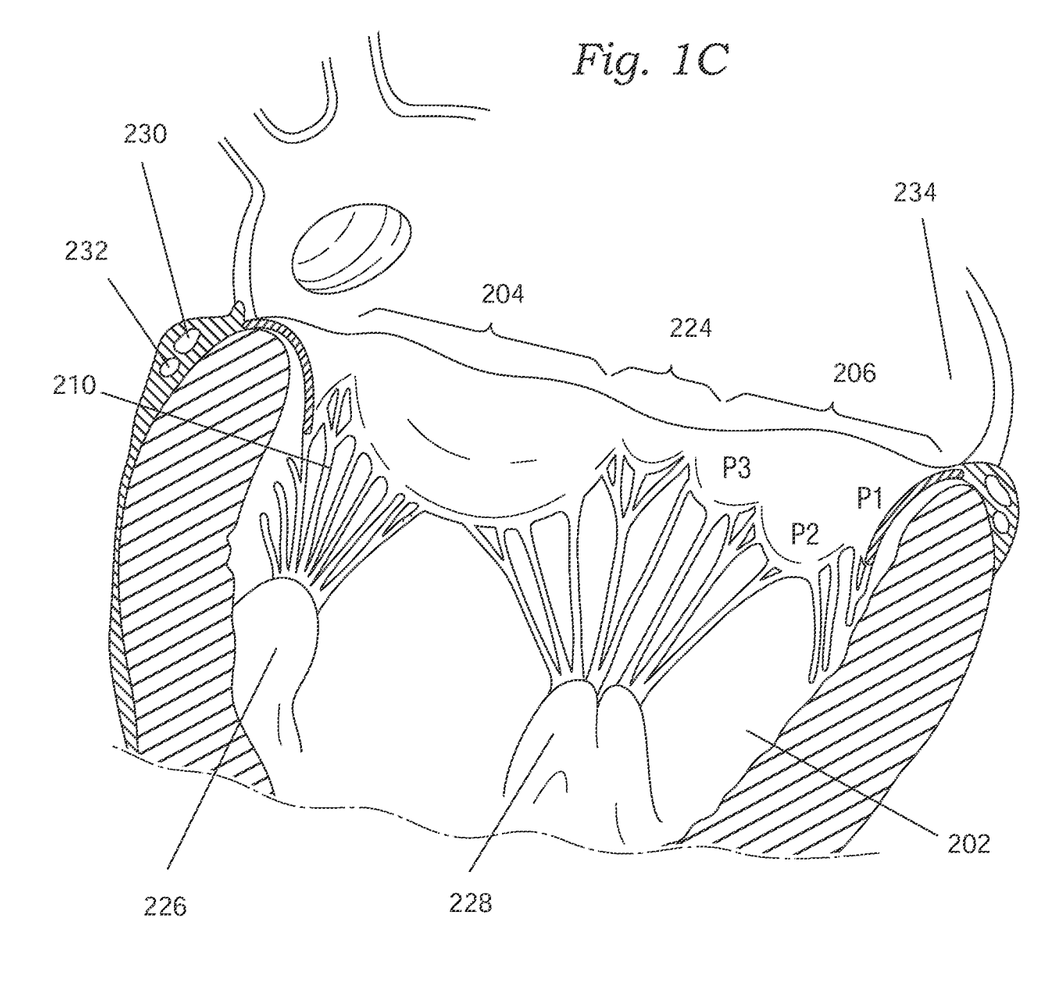
FIG. 1C is a laid-flat diagram of the mitral valve leaflets and subvalvular structure with anatomical descriptors.

FIG. 1C is a laid-flat diagram of the mitral valve leaflets 204, 206 and subvalvular structure with anatomical descriptors. In particular, the free edges of both the anterior leaflet 204 and posterior leaflet 206 (as well as the commissure leaflet 224 if present) connect to the chordae tendineae 210 and then to the subvalvular papillary muscles. There are two papillary muscles—an anterolateral and a posteriormedial papillary muscles 226, 228. The chordae tendineae extending upward from each of the papillary muscles connects to parts of both of the leaflets 204, 206. Also shown in the heart wall outside of the left ventricle 202 are the coronary sinus 230 and circumflex artery 232.

Figure 2A:
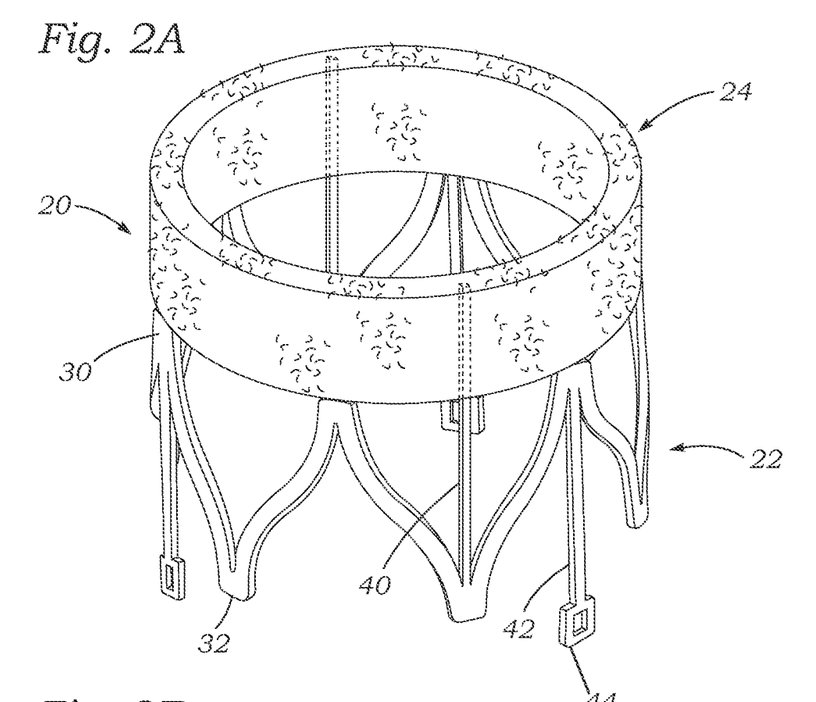
Figure 2B:
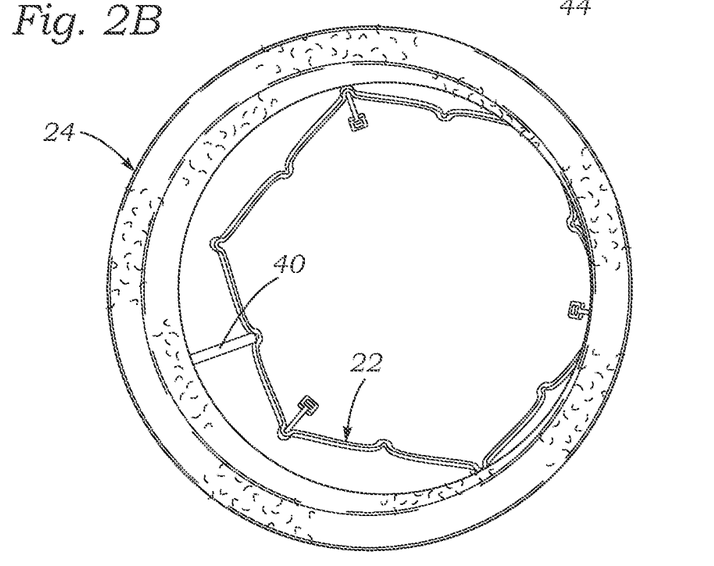
Figure 2C:
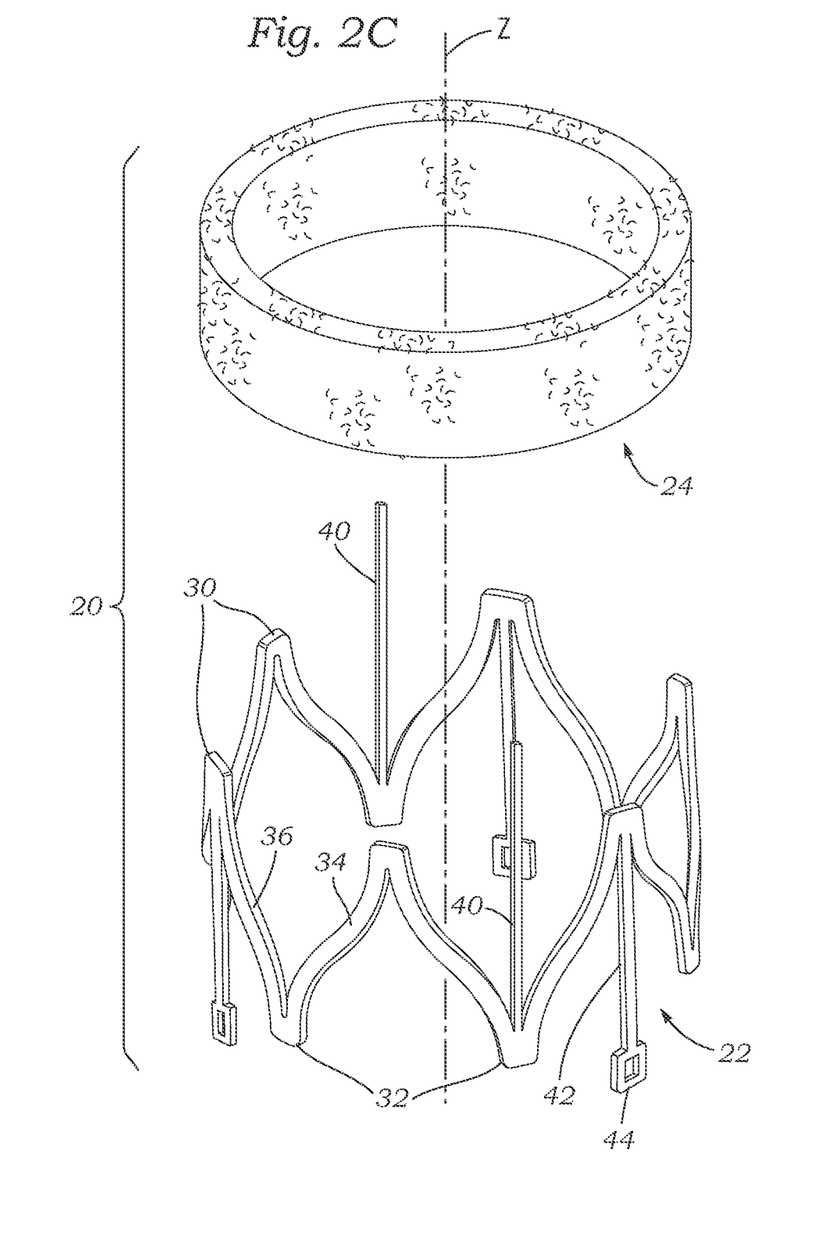
FIG. 2C is an exploded view thereof.

FIGS. 2A and 2B are side and top perspective views of an exemplary anchor device 20 of the present application having an undulating lower portion 22 (generally referred to as a "ventricular portion," but can be used in other locations) and a tubular leak-preventing upper portion 24 (generally referred to as an "atrial portion," but can be used in other locations), while FIG. 2C is an exploded view thereof.

The ventricular portion 22 of the illustrated anchor device 20 includes a plurality of peaks 30 evenly alternating with the same number of valleys 32 around its circumference, in an undulating fashion. In one exemplary embodiment there are six peaks 30 spaced 60° apart, each 30° separated from adjacent valleys 32. The peaks and valleys 30, 32 desirably lie in a tubular space such that the peaks 30 are positioned above the valleys 32 along a Z-axis, generally parallel to blood flow through the mitral valve when the device is implanted.

Descending and ascending circumferential struts 34, 36 connect each two adjacent peaks 30 and valleys 32. More particularly, as viewed looking down along the axis Z, a first circumferential strut 34 extends clockwise (CW) down from each one of the peaks 30 to each one of the valleys 32, and a second circumferential strut 36 extends up from the valley CW to the next peak. The circumferential struts 34, 36 can be generally S-shaped, with two distinct curvatures separated by a point of inflection. More specifically, each of the struts 34, 36 can terminate at its corresponding peak and valley in an asymptotic manner such that it is nearly aligned with the vertical Z-axis. Looking at one of the circumferential struts 34 extending between the peak 30 and the valley 32 in FIGS. 2A-2C, a first segment initially extends downward in a nearly vertical direction and has a concave up curvature until a point of inflection at a midpoint of the strut. From there, a second segment is curved concave down until it is nearly vertical at the valley 32. The second circumferential struts 36 can have a similar or different shape. The struts 34, 36 can be deployed such that they are in direct contact with the native heart valve leaflets, as will be explained, and this S-shaped configuration enhances their ability to pinch or clamp a wide area of the leaflet against the expandable heart valve that is positioned within the leaflets.

In the illustrated embodiment of FIGS. 2A-2C, the peaks and valleys 30, 32 are identically-shaped, and have generally flat ends. Optionally, the peaks and valleys 30, 32 may be rounded or more pointed, and the peaks may be different shape than the valleys. For example, the peaks 30 may have a greater radii than the valleys 32, or vice versa. Additionally, the struts 34, 36 are generally identical and have a point of inflection mid-way along the Z-axis, though they can be asymmetric such that the peaks 30 appear longer than the valleys 32, or vice versa. The undulating shape of the ventricular portion 22 enables the anchor device 20 to fit partly to the outside of the mitral leaflets except at two locations as will be seen.

The ventricular portion 22 can connect to the atrial portion 24 via one or more upstanding commissure posts 40, e.g., one, two, three, or more upstanding commissure posts. In the illustrated embodiment, there are two posts 40 diametrically opposed from each other and extending upward from two of the valleys 32 located generally opposite from one another and between clamping portions of the ventricular portion 22, as will be described below. The posts 40 extend upward beyond the upper extent of the peaks 30, and can be embedded and secured within the tubular atrial portion 24. The atrial portion 24 can comprise an annular ring of porous material, such as polyester fabric, porous polymer material, ePTFE, or foam. Means to connect the commissure posts 40 to the atrial portion 24 can be with adhesive, sutures, latches, friction, etc. Optionally, the posts 40 may have barbs or roughness of some sort to enable simple frictional holding. Still further, the posts 40 may be cloth covered or have one or more eyelets and be sutured to the atrial portion 24.

The ventricular portion 22 can further include one or more downwardly extending legs 42 that terminate in buckles 44 to facilitate manipulation and deployment of the anchor device 20. In the illustrated embodiment, the buckles 44 form squares or rectangles with a hole therethrough. The buckles 44 can be integrally formed with the ventricular portion 22 and preferably extend downward from one or more of the peaks 30. The term "integrally formed" in this regard means that the buckles 44 are either formed homogeneously with the rest of the ventricular portion 22 as a single piece, or that the buckles are secured to the ventricular portion 22 in a manner which enables manipulation of the buckles to manipulate the inner body. For example, the buckles 44 may be welded to the ventricular portion 22 after fabrication of both.

Figure 3A:
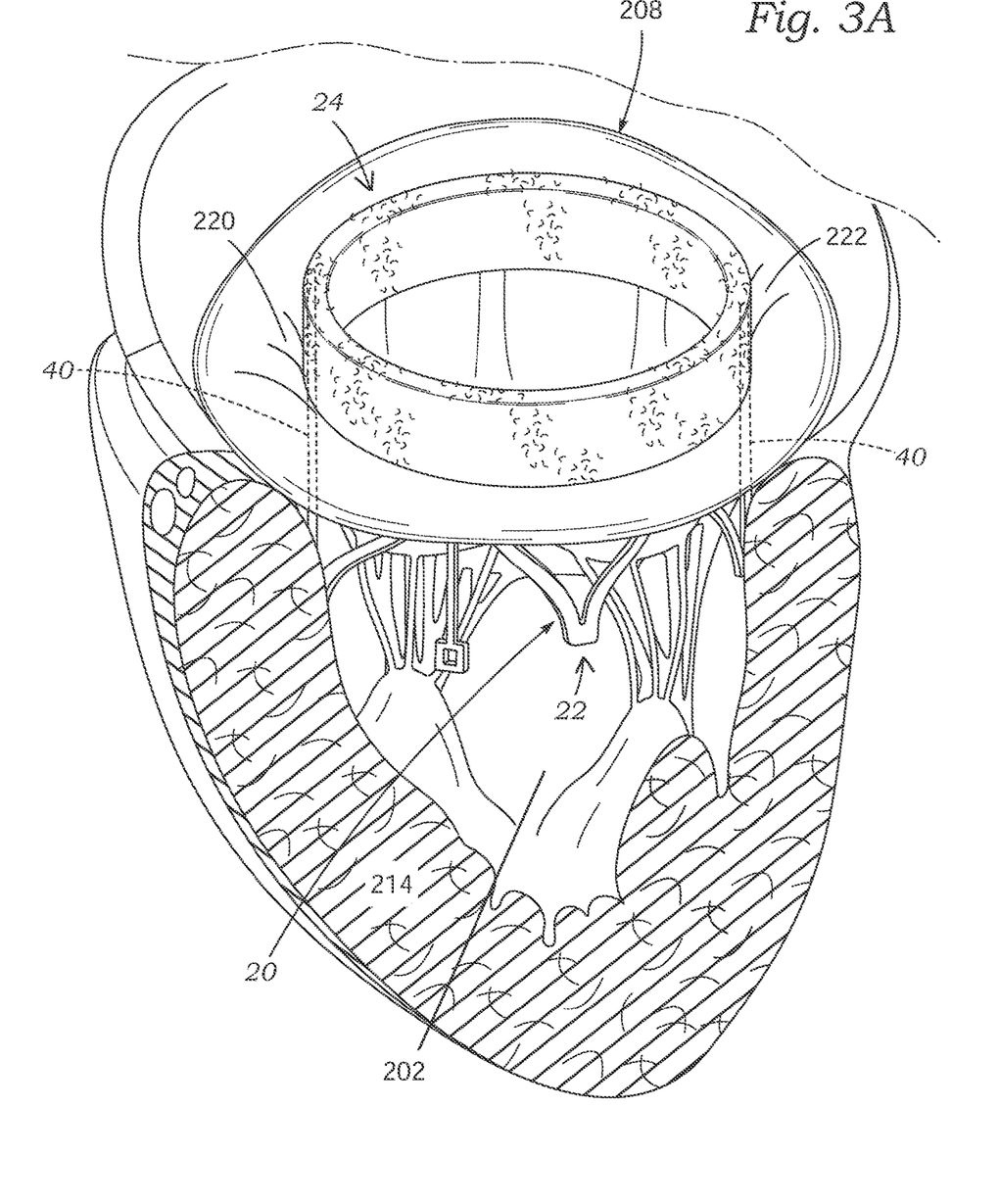
FIG. 3A is a schematic perspective view of the mitral valve similar to FIG. 1A that shows the position of the anchor device when deployed.

Now with reference to FIG. 3A the anchor device 20 is shown deployed at the mitral valve with the ventricular portion 22 below the mitral annulus 208 and the atrial portion 24 located above the annulus. The upstanding commissure posts 40 connect the two portions, and extend across the mitral annulus 208 at the anterior commissure 220 and posterior commissure 222.

Figure 3B:
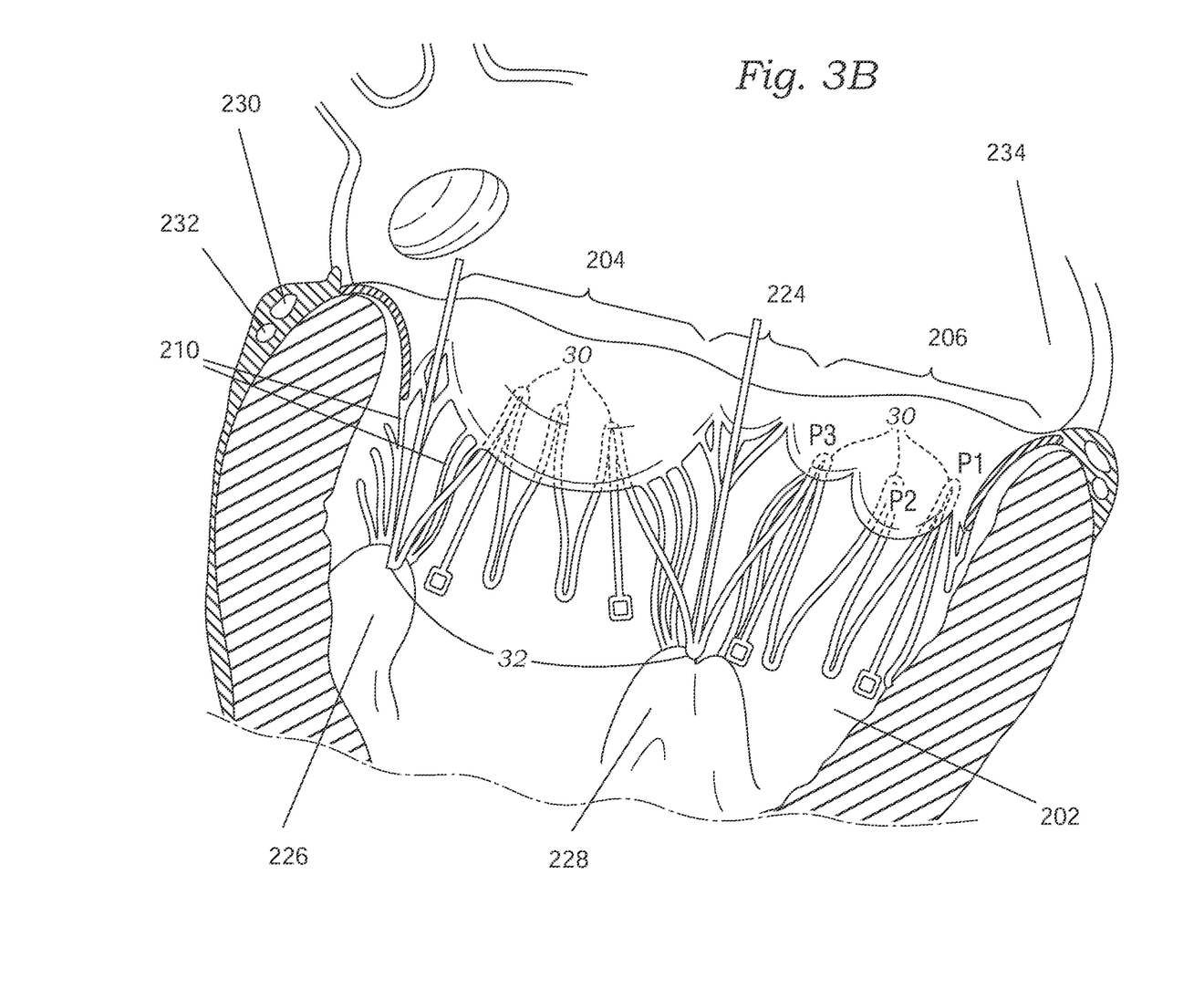
FIG. 3B is a laid-flat diagram of the mitral valve and a portion of the deployed anchor device.

FIG. 3B is a laid-flat diagram of the mitral valve and deployed anchor device 20 (with the atrial portion 24 removed for clarity). As mentioned, the undulating shape of the ventricular portion 22 enables the anchor device 20 to fit partly to the outside of the mitral leaflets 204, 206 except at the two commissure posts 40. That is, all three of the peaks 30 of the ventricular portion 22 are outside the leaflets, while the valleys 32 from which the commissure posts 40 extend upward are inside the leaflets. In this way, the commissure posts 40 can extend upward at the two valve commissures 220, 222 to support the atrial portion 24 above the annulus. At the same time, the majority of the ventricular portion 22 lies outside of the leaflets in order to provide an anchor against which a subsequently deployed prosthetic valve may be secured. The portions of the ventricular portion 22 outside of the leaflets define clamping portions of the anchor device 20, and may have different configurations as described below. Further, the various anchor devices herein can include two clamping portions as shown or another number of clamping portions, e.g., one, three, or more. The ventricular portion 22 "undulates" in the sense only that the clamping portions rise up from the valleys 32 from which project the commissure posts 40. Once more, the valleys 32 from which the commissure posts 40 project are located between clamping portions.

An exemplary beating heart method of securing a prosthetic heart valve at the mitral valve 200 between the left atrium 234 and left ventricle 202 includes advancing the anchor device 20 to the mitral valve and expanding the ventricular portion 22 of the device in the left ventricle. Using forceps or other manipulation tools, the two leaflet clamping portions are positioned radially outside respective ones of the two leaflets 204, 206. The surgeon then positions the upstanding posts 40 such that they project upward at the two native valve commissures 220, 222 and support the atrial portion 24 above the mitral valve annulus in the left atrium. Subsequently, an expandable prosthetic heart valve is advanced to within the mitral valve leaflets 204, 206 and expanded to compress the leaflets outward against the two leaflet clamping portions of the device 20.

Figure 3C:
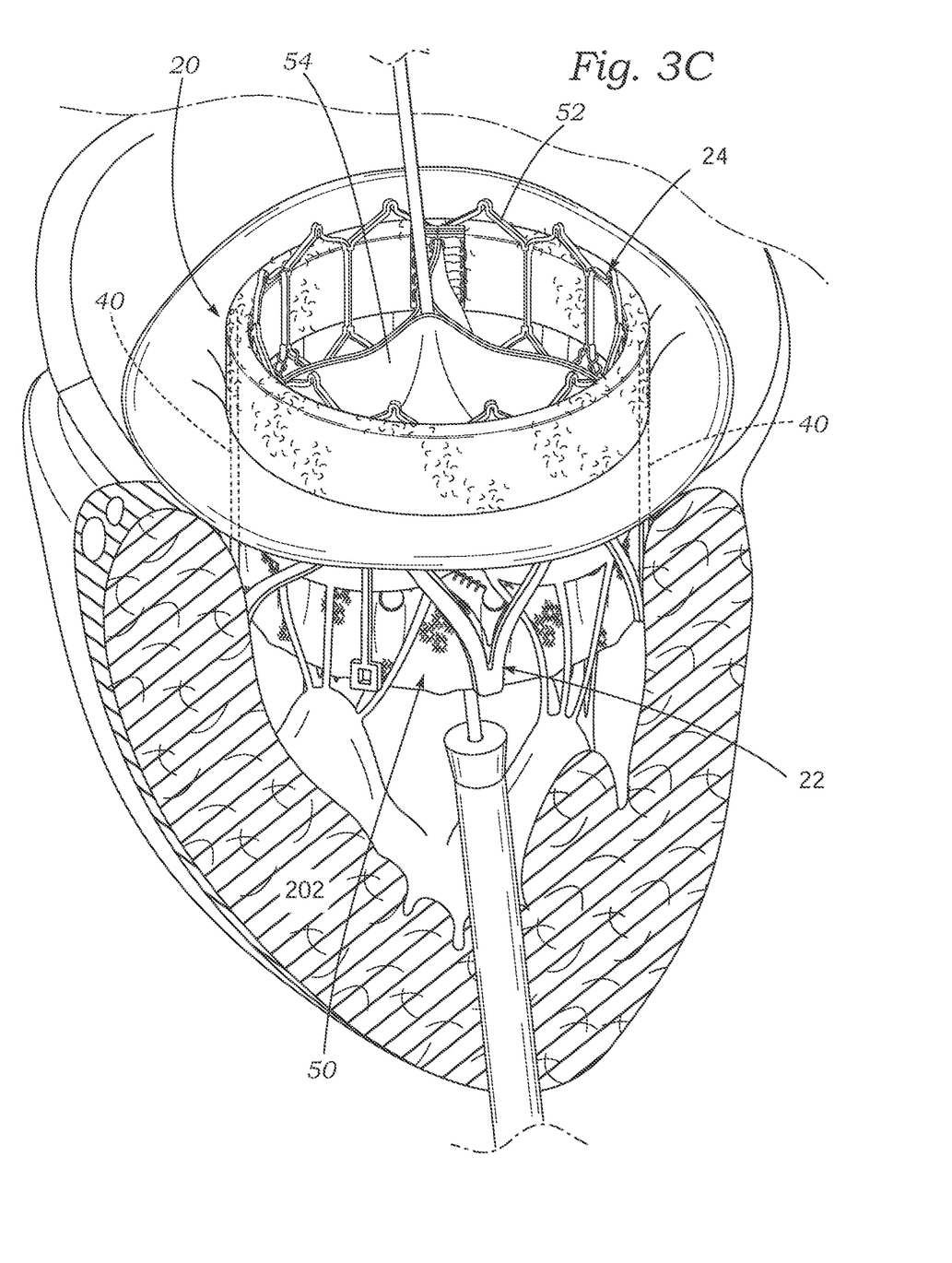
FIG. 3C is a schematic perspective view similar to FIG. 3A after delivery of a prosthetic heart valve within the anchor device.

FIG. 3C is a schematic perspective view similar to FIG. 3A after delivery of a prosthetic heart valve 50 within the anchor device 20. As mentioned, the prosthetic heart valve 50 is outwardly expandable and sandwiches the mitral leaflets 204, 206 against the inner surfaces of the clamping portions of the ventricular portion 22. As mentioned above, the prosthetic heart valve 50 may be constructed in a variety of ways, and can include an expandable structural stent or frame 52 that supports flexible leaflets 54, such as bovine pericardial leaflets. A top edge of the frame 52 can be deployed such that it terminates within the anchor device 20, and as shown ends within the atrial portion 24. The ventricular portion 22 of the anchor device 20 has sufficient hoop strength to provide a robust inward reaction force against the expandable frame 52, which in turn provides sufficient compression of the mitral leaflets 204, 206 to retain the valve 50 in place. The flexible leaflets 54 of the prosthetic heart valve 50 then function normally and replace the native leaflets.

FIGS. 4A-4D are exemplary leak-preventing atrial portions that can be used with the anchor devices described herein. For example, the tubular atrial portion 24 shown above can be replaced with smaller structures that either provide a plug of sorts at the native valve commissures 220, 222 and/or exert a pinching force to the two mitral leaflets 204, 206 at the commissures, in both cases helping to reduce regurgitation of blood upward around the prosthetic heart valve 50 (termed "paravalvular leakage").

Figure 4A:
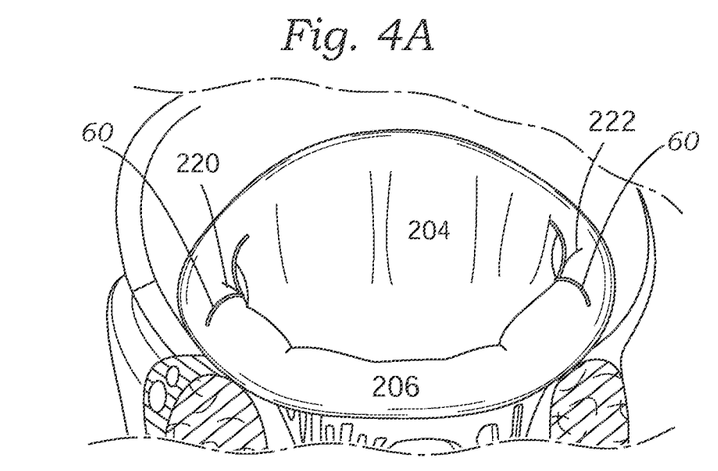
FIGS. 4A-4D are exemplary leak-preventing atrial portions that can be used with the anchor devices described herein.
Figure 4B:
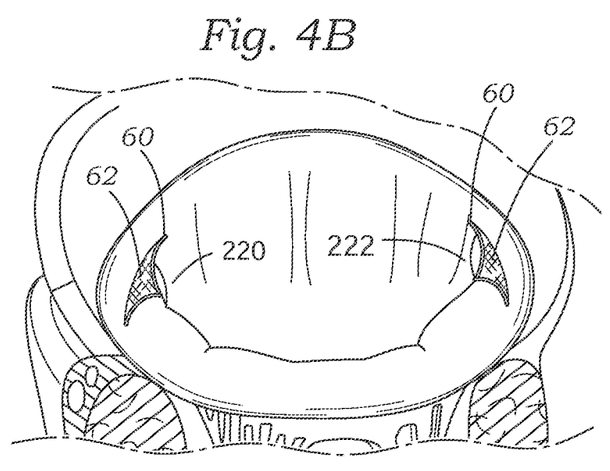

For instance, FIG. 4A shows a pair of Y-shaped struts 60 formed on upper ends of the vertical posts 40. The struts 60 extend on the atrial side of the valve commissures 220, 222 and curl around to contact and urge the outer extents of the mitral leaflets 204, 206 toward each other, thus closing off any opening that may form outside of the prosthetic heart valve 50 at the native commissures. FIG. 4B is a similar structure wherein a small fabric cover 62 is added across the Y-shaped struts 60, which further helps close off any blood leakage.

Figure 4C:
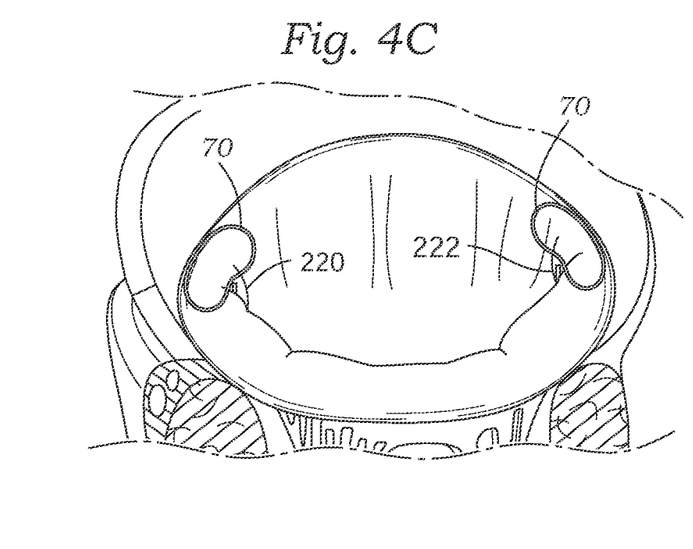
Figure 4D:
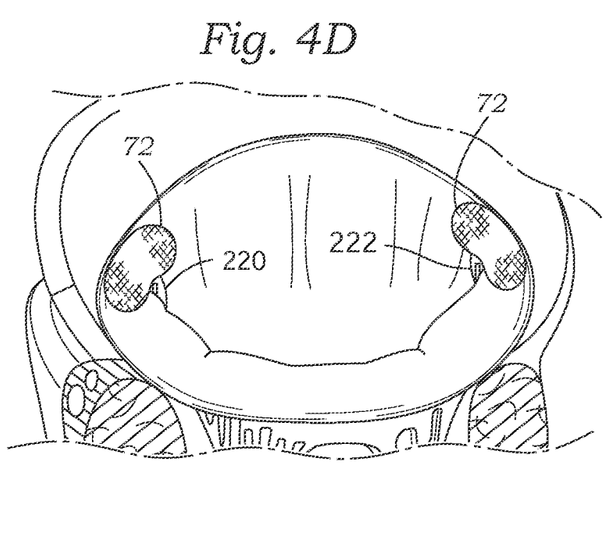

FIG. 4C shows an alternative embodiment where a wire ring 70 is provided at the tops of each of the posts 40. The wire ring 70 may be Nitinol and shaped to apply a compressive force to the mitral leaflets 204, 206 at the native valve commissures 220, 222, which helps close any gap that may permit leakage. FIG. 4D shows the same wire ring 70 on each post 40 having a mesh or fabric cover 72 secured thereto. The cover 72 may be a braided metallic screen or a polymer fabric, and further assists in reducing paravalvular leakage.

Figure 5:
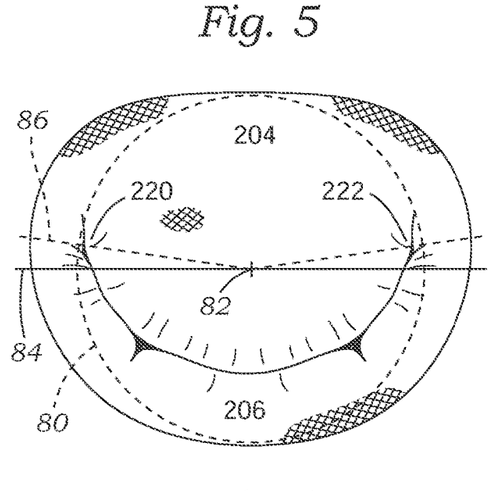
FIG. 5 is an atrial plan view of the mitral valve leaflets indicating an exemplary dashed line outline for an anchor device as described herein.

FIG. 5 is an atrial plan view of the mitral valve leaflets 204, 206 indicating an exemplary circular dashed line outline 80 for an anchor device as described herein. A center point 82 of the outline 80 may be drawn, as well as a horizontal axis 84 through the center, roughly oriented along a major axis of the mitral valve annulus. That is, the mitral valve annulus typically presents as D- or kidney bean-shaped, or at least oval, with a longer dimension perpendicular to a shorter dimension. The shorter dimension, or minor axis, roughly bisects the two mitral leaflets 204, 206. Due to the mismatch of a circular anchor device expanded within the irregular-shaped mitral valve annulus, the horizontal axis 84 along a diameter of the anchor device will not likely intersect the native valve commissures 220, 222. Two dashed lines 86 have been drawn from the center point 82 through the commissures 220, 222. Since the upstanding vertical posts connecting the ventricular and atrial portions of the anchor device must pass through and therefore align with the commissures 220, 222, they may be positioned around the anchor device offset from the horizontal axis 84, and in particular along the dashed lines 86.

Figure 6:
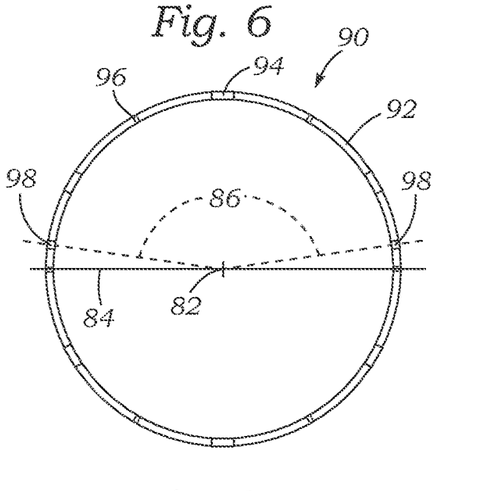
FIG. 6 is a plan view of just a lower or ventricular portion of an anchor device configured to match the dashed line outline of FIG. 5.

FIG. 6 is a top plan view of just a ventricular portion of an anchor device 90 configured to match the dashed line outline of FIG. 5. The anchor device 90 may be constructed the same as that described above, such that a series of struts 92 define peaks 94 intermediate valleys 96. Two upstanding posts 98 project upward at two of the valleys 96, as before, but are located slightly offset from the horizontal axis 84 as shown in FIG. 5 and represented in FIG. 6. The dashed lines 86 are also shown and pass through the upstanding posts 98. That is, the two upstanding posts 98 are located less than 180° from each other around a circumference of the anchor device 20. The angular offset of each of the upstanding posts 98 defined by the angle made by the dashed lines 86 with the horizontal axis 84 is desirably between about 5-15°. In other words, the two upstanding posts 98 are located between 150-170° from each other around a circumference of the anchor device 20. This ensures that the upstanding posts 98 more closely coincide with the location of the native valve commissures 220, 222 so as to limit deformation of the mitral annulus when the anchor device 90 is implanted.

Figure 7:
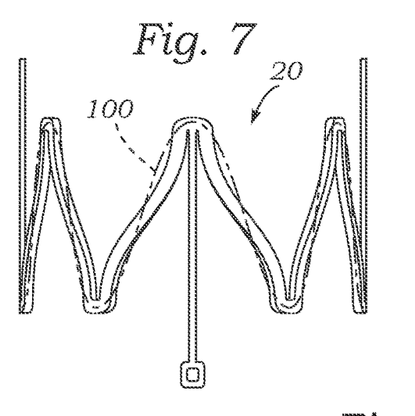
FIG. 7 is an elevational view of the lower or ventricular portion of an exemplary anchor device with an undulating dashed line superimposed thereon.

FIG. 7 is an elevational view of the ventricular portion of the exemplary anchor device 20 with an undulating dashed line 100 superimposed thereon. The dashed line 100 has a sinusoidal shape to illustrate the basic undulations of the struts of the anchor device 20.

Figure 8:
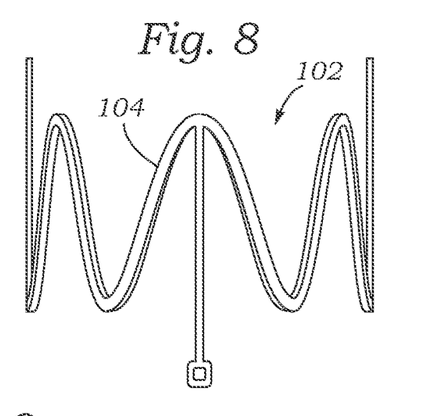
FIG. 8 is an elevational view of the lower or ventricular portion of an alternative anchor device shaped like the undulating dashed line from FIG. 7.

FIG. 8 is an elevational view of the ventricular portion of an alternative anchor device 102 with struts 104 shaped like the undulating dashed line 100 from FIG. 7. In this configuration all peaks and valleys have rounded ends to help reduce any sharp edges and possible abrasion of the mitral leaflets.

Figure 9:
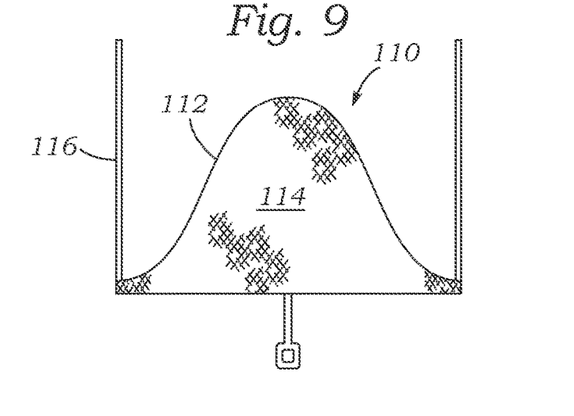
FIG. 9 is an elevational view of the lower or ventricular portion of a further exemplary anchor device having an undulating shape and a fabric cover.

FIG. 9 is an elevational view of the ventricular portion of a further alternative anchor device 110 having undulating struts 112 and a fabric cover 114. The number of peaks and valleys are reduced to a minimum of one peak between the valleys from which upstanding posts 116 originate. This shows one extreme of the shape of the clamping portion of the anchor device 110, and illustrates what is meant by undulating. Namely, the anchor devices undulate between the clamping portions and the valleys from which the upstanding posts 116 project. This enables the upstanding posts 116 to be located within the mitral leaflets so as to be able to extend up to the atrial side thereof. At the same time, the clamping portions rise up and can be positioned to the outside of the mitral leaflets for clamping engagement with the prosthetic valve. The clamping portions can include just one peak or upward bend, or multiple peaks as in FIGS. 7 and 8. The fabric cover 114 can extend across multiple peaks and help avoid tangling with the chordae tendineae. The alternating peaks and valleys permit the anchor devices to be constricted into a small diameter profile for delivery through an access tube or sheath, but other compressible structures are contemplated.

While the invention has been described in terms of particular variations and illustrative figures, the invention is not limited to the variations or figures described. The features described with respect to one embodiment or variation may be used in other embodiments or variations. Methods described separately may be combined. In addition, where methods and steps described above indicate certain events occurring in certain order, the ordering of certain steps can be modified and that such modifications are in accordance with the variations of the invention. Additionally, certain of the steps may be performed concurrently in a parallel process when possible, as well as performed sequentially as described above. Many modifications can be made to adapt a particular situation or device to the teachings of the invention without departing from the essential scope thereof. Therefore, it is intended that the invention not be limited to the particular embodiments disclosed herein, and to the extent there are variations of the invention, which are within the spirit of the disclosure or equivalent to the inventions found in the claims, it is the intent that this patent will cover those variations as well.

What is claimed is:

1. A beating heart method of securing a prosthetic valve at a native valve between an atrium and a ventricle, the native valve having native leaflets and attached chords in the ventricle, and commissures between the leaflets at a native annulus of the native valve, comprising:

advancing an anchor device to the native valve, the device having a ventricular portion and an atrial portion, the ventricular portion having an expandable tubular body about a vertical axis comprising undulating struts, the tubular body having two leaflet clamping portions opposite one another each defined by at least one peak and two valleys, the device further including two upstanding vertical posts each commencing at a separate valley of the undulating struts and extending upward beyond a maximum height of the peaks of the two leaflet clamping portions and terminating in the atrial portion;

expanding the ventricular portion of the device in the ventricle and positioning the two leaflet clamping portions radially outside respective leaflets of the native leaflets;

positioning the upstanding posts such that they project upward at the valve commissures and support the atrial portion above the native annulus in the atrium; and advancing an expandable prosthetic valve to within the native leaflets and expanding to compress the native leaflets outward against the two leaflet clamping portions of the device.

2. The method of claim 1, wherein the anchor device and prosthetic valve are deployed using one access system.

3. The method of claim 1, wherein the anchor device and prosthetic valve are deployed using two separate access systems.

4. The method of claim 1, wherein the anchor device struts are Nitinol, and each clamping portion has at least two peaks and one valley therebetween.

5. The method of claim 1, wherein the clamping portions are covered with fabric.

6. The method of claim 1, wherein the atrial portion includes a tubular foam member.

7. The method of claim 1, wherein the atrial portion includes a pair of Y-shaped struts at a terminal end of each vertical post.

8. The method of claim 7, further including a fabric cover across each pair of Y-shaped struts.

9. The method of claim 1, wherein the atrial portion includes a wire ring at a terminal end of each vertical post.

10. The method of claim 9, further including a cover across the wire rings.

11. A beating heart method of securing a prosthetic valve at a native valve between an atrium and a ventricle, the native valve having native leaflets and attached chords in the ventricle, and commissures between the leaflets at a native annulus of the native valve, comprising:

advancing an anchor device to the native valve, the device having a lower portion and an upper portion, the lower portion having an expandable tubular body about a vertical axis comprising undulating struts, the tubular body having a leaflet clamping portion defined by at least one peak and valleys adjacent the at least one peak, the device further including an upstanding vertical post commencing at a valley of the undulating struts and extending upward beyond a maximum height of the at least one peak of the leaflet clamping portion and terminating in the upper portion;

expanding the lower portion of the device below the native valve annulus and positioning the leaflet clamping portion radially outside at least one leaflet of native leaflets of the native valve; and positioning the upstanding vertical post such that it projects upward at a native valve commissure and supports the upper portion above a native annulus of the native valve.

12. The method of claim 11, further comprising advancing an expandable prosthetic valve to within the native leaflets and expanding to compress the at least one leaflet outward against the leaflet clamping portion.

13. The method of claim 11, wherein the anchor device and prosthetic valve are deployed using one access system.

14. The method of claim 11, wherein the anchor device and prosthetic valve are deployed using two separate access systems.

15. The method of claim 11, wherein the anchor device struts are Nitinol, and the clamping portion has at least two peaks and one valley therebetween.

16. The method of claim 11, wherein the clamping portion is covered with fabric.

17. The method of claim 11, wherein the upper portion includes a tubular foam member.

18. The method of claim 11, wherein the upper portion includes a pair of Y-shaped struts at a terminal end of each vertical post.

19. The method of claim 18, further including a fabric cover across each pair of Y-shaped struts.

20. The method of claim 11, wherein the upper portion includes a wire ring at a terminal end of each vertical post and a cover across each of the wire rings.

\* \* \* \* \*